United States Patent [19]

N'Guyen

[11] Patent Number: 5,686,082
[45] Date of Patent: Nov. 11, 1997

[54] COSMETIC OR PHARMACEUTICAL COMPOSITION CONTAINING A COMBINATION OF A POLYPHENOL AND A GINKGO EXTRACT

[75] Inventor: Quang-Lan N'Guyen, Antony, France

[73] Assignee: L'Oreal, Paris, France

[21] Appl. No.: 290,897

[22] PCT Filed: Dec. 23, 1993

[86] PCT No.: PCT/FR93/01295

§ 371 Date: Oct. 19, 1994

§ 102(e) Date: Oct. 19, 1994

[87] PCT Pub. No.: WO94/14414

PCT Pub. Date: Jul. 7, 1994

[30] Foreign Application Priority Data

Dec. 24, 1992 [FR] France ................................. 92 15725

[51] Int. Cl.$^6$ ............................................... A61K 7/48
[52] U.S. Cl. ..................... 424/401; 424/450; 424/195.1; 514/844; 514/846
[58] Field of Search ........................... 424/401, 195.1, 424/450; 514/844, 846

[56] References Cited

U.S. PATENT DOCUMENTS

| | | | |
|---|---|---|---|
| 4,289,495 | 9/1981 | Bugaut et al. ........................ | 8/406 |
| 5,043,323 | 8/1991 | Bombardelli et al. ................ | 514/25 |
| 5,114,716 | 5/1992 | N'Guyen et al. ..................... | 424/401 |

FOREIGN PATENT DOCUMENTS

| | | |
|---|---|---|
| 0275005 | 7/1988 | European Pat. Off. . |
| 0307626 | 3/1989 | European Pat. Off. . |
| 0353161 | 1/1990 | European Pat. Off. . |
| 0496173 | 7/1992 | European Pat. Off. . |
| 2400358 | 3/1979 | France . |
| 2667505 | 4/1992 | France . |

OTHER PUBLICATIONS

Morelle, "Que peuvent nous apported les extraits vegetaux?: Le ginkgo biloba", Parfums, Cosmetiques et Aromes, vol. 96, 1991, pp. 77–86.

Matsui, "Manufacture of extract with high content of flavonoids from gingko leaves", Chemical Abstracts, vol. 116 No. 4, 1992, Abstract No. 28119h.

*Primary Examiner*—Jyothsan Venkat, Ph.D.
*Attorney, Agent, or Firm*—Nixon & Vanderhye, P.C.

[57] ABSTRACT

A cosmetic or pharmaceutical composition containing a synergistically active oxidation inhibiting system consisting of a combination of a ginkgo extract and at least one polyphenol compound. For example, the ginkgo extract may be a hexane extract of ginkgo leaves and the polyphenol compound may be a flavonoid. Said composition may be used to prevent and treat cell damage on the skin, scalp or mucosae by free radicals induced especially by atmospheric pollutants and/or ultraviolet radiation, and/or for controlling the phenomenon of accelerated skin ageing.

14 Claims, No Drawings

COSMETIC OR PHARMACEUTICAL COMPOSITION CONTAINING A COMBINATION OF A POLYPHENOL AND A GINKGO EXTRACT

The subject of the invention is a cosmetic or pharmaceutical composition containing, as antioxidizing agent, a combination, possessing a synergistic action, of a ginkgo extract and at least one polyphenol derivative.

The majority of cosmetic or pharmaceutic compositions consists of a fatty phase, the oily products of which have a certain tendency to oxidize, even at room temperature. This oxidation has the consequence of profoundly modifying the properties, especially olfactive, which makes them unusable after a variable period of time.

In order to protect the compositions with respect to these oxidation phenomena, it is common practice to incorporate protective agents which act as antioxidizing agents.

While antioxidizing agents are particularly useful for the good preservation of fats in cosmetic or pharmaceutical compositions, it is now known that some of them also make it possible to control the harmful effects of oxidizing substances, formed under the action of free radicals generated especially by atmospheric pollutants and ultraviolet radiation. These harmful effects are exerted in particular on the cells of the skin and of the mucous membranes in contact with the external environment.

It is thus important to be able to have available antioxidizing agents capable of inhibiting formation of free radicals and which make it possible to control oxidation phenomena which can cause irreversible cell damage.

It has now been discovered that it was possible both to obtain good preservation of cosmetic or pharmaceutical compositions containing easily oxidizable fats and to efficiently protect the skin or the mucous membranes by using a combination of a ginkgo extract and at least one polyphenol compound. It has additionally been discovered that this combination surprisingly possesses synergistic properties.

The expression "polyphenol compound" is understood to mean compounds containing at least one diphenol aromatic ring, it being possible for the phenol groups to be optionally etherified or esterified. In what follows, such a compound can also be called simply "polyphenol".

The subject of the invention is thus a cosmetic or pharmaceutical composition containing an antioxidizing system possessing a synergistic action consisting of the combination of a ginkgo extract and at least one polyphenol compound.

The active substance (or the active substances) of the ginkgo extract is not known but this active substance can be obtained by extracting the plant matter, and especially the leaves, using a nonpolar solvent. The expression "nonpolar extract" hereinafter denotes either such an extract or one or more active substances contained in such an extract and which can be isolated therefrom by a more exhaustive purification. An active substance here denotes a substance having an antioxidizing activity (which can be revealed, for example, according to a self-oxidation test of vitamin F as described in the experimental part below) and whose combination with a polyphenol makes it possible to reveal a synergistic antioxidizing action.

An extract from Ginkgo biloba leaves is especially used.

The nonpolar ginkgo extract can be obtained by evaporating to dryness fractions resulting from extraction of ginkgo leaves with a nonpolar solvent. Linear, branched or cyclic $C_6$–$C_{14}$ alkanes may be mentioned as nonpolar solvent, n-hexane being particularly preferred. Such extracts are described especially in Japanese Patent 91-014,007.

The polyphenol compounds used in the composition of the invention can be chosen from those which have an antioxidizing activity in a self-oxidation test of vitamin F as described below in the experimental part.

The polyphenol can be chosen, for example, from:
a) flavonoids
b) carnosic acid or carnosol
c) optionally substituted 2,5-dihydroxybenzoic and (2,5-dihydroxyphenyl)alkylenecarboxylic acids and their derivatives, especially their salts, esters or amides,
d) esters or amides of caffeic acid,
e) tannic acid.

Mention will be made, among the polyphenols which can be used, of especially flavonoids corresponding to the general formula (I):

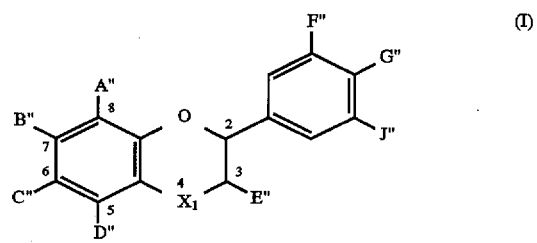

or (II):

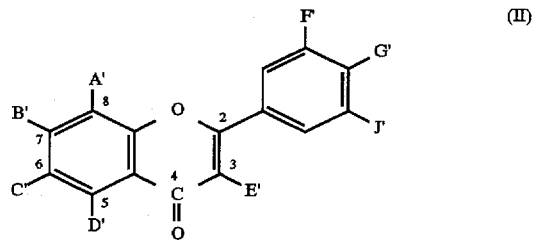

in which A", B", C" and D", independently of one another, represent H or OH; E" represents H, OH or OX', where X' represents:

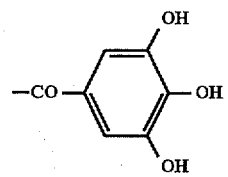

F", G" and J" represent, independently of one another, H or OH; and $X_1$ represents —$CH_2$—, —CO— or —CHOH—, A', C' and D', independently of one another, represent H, OH or $OCH_3$;

E' represents H, OH or OR', where R' represents the residue of a sugar of formula R'OH;

B', F', G' and J', independently of one another, represent H, OH, $OCH_3$ or —$OCH_2$—$CH_2$—OH. Rutinose may be mentioned among the sugars R'OH.

The compounds of formulae (I) and (II) are known. They can be obtained especially according to the processes described in "The Flavonoids", Harborne J. B., Mabry T. J., Helga Mabry, 1975, pages 1 to 45.

Among the flavonoids which can be used according to the invention, mention will especially be made of taxifolin, catechin, epicatechin, eriodictyol, naringenin, rutin, troxerutin, chrysin, tangeretin, luteolin, epigallocatechin and epigallocatechin gallate, quercetin, fisetin, kaempferol, galangin, gallocatechin and epicatechin gallate.

Certain polyphenols which can be used are present in plants from which they can be extracted in a known way. It is possible to use extracts from tea leaves (Camellia sinensis or Camellia japonica). Mention will in particular be made of the green tea extracts sold under the name SUNPHENON® by the Company Nikko, which especially contain flavonoids.

Among polyphenols which can be used, mention will also be made of the polyphenols such as carnosic acid and carnosol which can be extracted, for example, from rosemary, either by extraction followed by distillation (Chang etal., JOSC, Vol. 61, No. 6, June 1984) or by extraction with a polar solvent such as ethanol preceded by extraction using a nonpolar solvent such as hexane to remove the odorant substances, as described in Patent Application EP-307,626.

The polyphenols which can be used can also be chosen from (2,5-dihydroxyphenyl)alkylenecarboxylic acids of formula (III) and their derivatives (especially esters and amides):

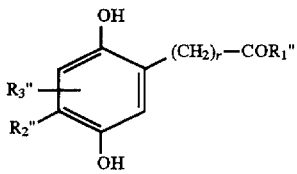

in which:

R"$_1$ represents —O—Alk, OH or —N(r')(r"), Alk being a linear or branched $C_1$–$C_{20}$ alkyl, optionally substituted by one or more hydroxyl or alkoxy groups, or Alk being a $C_2$–$C_{20}$ alkenyl, r' and r" independently represent H, $C_1$–$C_{20}$ alkyl, $C_2$–$C_6$ hydroxyalkyl or $C_3$–$C_6$ polyhydroxyalkyl, or alternatively r' and r" form, together with a nitrogen atom to which they are attached, a heterocycle, r is a number, including zero, such that the —(CH$_2$)$_r$—COR$_1$ chain contains at most 21 carbon atoms, R"$_2$ and R"$_3$ independently represent H or a $C_1$–$C_4$ alkyl, it additionally being possible for R"$_2$ to represent a $C_1$–$C_4$ alkoxy.

The compounds of formula (III) are known or can be prepared according to known methods, for example analogous to those described in Patents FR-2,400,358 and FR-2,400,359.

Among the polyphenols which can be used according to the invention, mention will also be made of the esters or amides of caffeic acid. Among the esters of caffeic acid, mention may especially be made of the compounds of formula (IV):

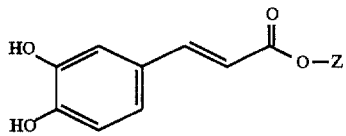

in which Z represents a $C_1$–$C_8$ alkyl, for example methyl, or the residue of a phytol.

Among the amides of caffeic acid, mention may especially be made of the compounds of formula (V):

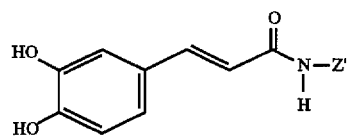

in which Z' represents a $C_1$–$C_8$, in particular $C_6$–$C_8$, alkyl.

The compounds of formula (IV) or (V) are known or can be prepared according to known methods.

Tannic acid is present especially in the nutgall extract marketed under the name SUPEXTRAT® by the Company Sochiho.

In the cosmetic or pharmaceutical compositions according to the invention, the nonpolar ginkgo extract is generally present at a concentration of between 1 and 10% by weight with respect to the total weight of the composition.

The polyphenol as defined above is present in a proportion of between 0.1 and 1% by weight with respect to the total weight of the composition.

The optimum relative proportions of nonpolar ginkgo extract and of polyphenol can be determined for each type of composition by simple routine experiments. The ratio by weight of the nonpolar ginkgo extract to the polyphenol is generally between 1 and 100, and in particular in the region of 10.

The cosmetic or pharmaceutical compositions of the invention can contain, besides the combination of active principles described above, and a suitable vehicle, the ingredients or adjuvants commonly used in producing such compositions. They can contain, in particular, solvents such as water, organic solvents (alcohols or oils, for example) or silicones, thickening agents, surface-active agents, polymers, solid fats (waxes or lanolin, for example), moistening agents, preserving agents, pH modifying agents, sequestering agents, coloring agents, fragrances, solid fillers (powders and pigments), ultraviolet-absorbing substances, instant tanning agents (such as dihydroxyacetone), and the like.

The compositions in the form of vesicular dispersions contain, for example, at least one active ingredient incorporated in lipid double-layers or micelles, which can encapsulate an aqueous phase, and dispersed in an aqueous solvent.

The lipid vesicular dispersions, especially of ionic or non-ionic amphiphilic lipids, are prepared according to known processes, for example by swelling the lipids in an aqueous solution in order to form spherules dispersed in the aqueous medium, as described in the article by Banghan, Standish and Watkins, J. Mol. Biol., 13, 238 (1965) or in Patents FR 2,315,991 and 2,416,008. The description of various methods of preparation will also be found in "Les liposomes en biologie cellulaire et pharmacologie" [Liposomes in cell biology and pharmacology], published by INSERM/John Libbery Eurotext, 1987, pages 6 to 18.

The compositions can be provided in the form of dispersions of nanoparticles. The term "nanoparticles" covers, on the one hand, nanospheres and, on the other hand, nanocapsules; the term "nanospheres" denotes nanoparticles consisting of a porous polymer matrix on which the active principle is absorbed and/or adsorbed and the term "nanocapsules" denotes nanoparticles consisting of a polymer membrane which surrounds a core formed by the active principle. Such composition forms are described, for example, in Patent Applications EP-274,961 and FR-2,659,554.

The compositions of the invention are especially cosmetic or pharmaceutical compositions which protect human skin, hair and mucous membranes, compositions for making up the skin and exoskeleton compositions having an oral hygiene use such as toothpastes, or ophthalmic compositions such as eye washes.

When the cosmetic composition according to the invention is used to protect hair, it can be provided in the form of shampoos, lotions, gels or rinsable compositions, to be applied before or after a shampoo, before or after dyeing or bleaching, or before, during or after a permanent Wave or hair straightening treatment. It can additionally be provided in the form of styling or treating gels or lotions, of lotions or gels for blow drying or hair setting, of hair lacquers, of permanent wave or hair straightening compositions or hair dyeing or hair bleaching compositions.

When the composition of the invention is used as a product for making up eyelashes, eyebrows or the skin, it is provided, for example, in the form of skin treatment or foundation creams, lipsticks, eyeshadows, blushers, eye liners or mascaras.

When the composition of the invention is a pharmaceutical composition, it can be provided especially in the emulsion (milk or cream), gel, lotion, ointment, vesicular dispersion or nanoparticle dispersion form, and can contain, besides the combination described above, another pharmaceutical active principle.

By virtue of the synergistic combination which they contain, the compositions of the invention constitute cosmetic or pharmaceutical compositions intended to be applied especially to the skin, exoskeleton and mucous membranes which make it possible, for example, to prevent or treat damage caused by free radicals induced especially by atmospheric pollutants and by ultraviolet radiation. In particular, the cosmetic compositions of the invention make it possible to prevent or treat the phenomenon of accelerated skin ageing.

Another subject of the invention is the use of a combination of at least one ginkgo extract and at least one polyphenol, as synergistic active combination, in the preparation of a cosmetic or pharmaceutical composition intended to prevent or treat cell damage caused, on the skin, scalp or mucous membranes, by free radicals induced especially by atmospheric pollutants and/or by ultraviolet radiation, and/or intended to control the phenomenon of accelerated skin ageing.

Another subject of the invention is a cosmetic treatment process which makes it possible to control damage, giving an unpleasant appearance to the skin or hair, caused by free radicals induced especially by atmospheric pollutants and by ultraviolet radiation, characterized in that a composition containing the synergistic combination which has been described above is applied to the skin or hair.

The following examples illustrate the invention.

In these examples, the ginkgo extracts used were prepared in the way shown below. The green tea extract SUNPHENON® is marketed by Nikko Chemicals. The aqueous/alcoholic nutgall extract is marketed by Sochibo under the name SUPEXTRAT®.

METHOD OF OBTAINING GINKGO EXTRACTS

Ginkgo biloba leaves, reduced to the form of a plant powder, are introduced into a cartridge made of porous cellulose cardboard.

The cartridge is introduced into a "Soxhlet"-type extractor: this extractor is equipped at its base with a round-bottomed flask containing hexane heated to boiling point (69° C.). The solvent vapors pass through a diversion, are condensed in the reflux condenser and fall back in the liquid state into the cartridge, progressively immersing the latter. After total immersion, the solvent, laden with plant extracts, flows out by syphoning into the starting round-bottomed flask. The process is carried on continuously, the liquid in the round-bottomed flask being increasingly laden with plant extracts.

Extraction is carried out for 12 hours.

The hexane fractions are then evaporated to dryness under reduced pressure.

EXAMPLE 1: O/W Body Lotion

This lotion has the following composition (% by weight):

| | |
|---|---|
| Glyceryl stearate | 2% |
| TWEEN 60 ® (sorbitan monostearate containing 20 mol of ethylene oxide) sold by the Company ICI | 1% |
| Stearic acid | 1.4% |
| Triethanolamine | 0.7% |
| CARBOPOL 940 ® (neutralized by triethanolamine) | 0.2% |
| Oil of sweet almonds | 3% |
| Liquid paraffin | 8% |
| Aqueous/alcoholic nutgall extract | 0.1% |
| Ginkgo extract | 1% |
| Sterile demineralized water + preserving agents q.s. for | 100% |

O/W means: emulsion of oil-in-water type.

CARBOPOL 940® is a crosslinked polyacrylic acid sold by Goodrich.

The glyceryl stearate, TWEEN 60®, stearic acid and oils are heated to 75°–80° C. The triethanolamine is added. This mixture is poured into the neutralized CARBOPOL® in the presence of 60 g of water. The temperature is lowered to 40° C. The extracts, remaining water and preserving agents are incorporated.

EXAMPLE 2: O/W Bodycare cream

The following cream was prepared analogously:

| | |
|---|---|
| Glyceryl stearate | 2% |
| TWEEN 60 ® (sorbitan monostearate containing 20 mol of ethylene oxide) sold by the Company ICI | 1% |
| Cetyl alcohol | 0.5% |
| Stearic acid | 1.4% |
| Triethanolamine | 0.7% |
| CARBOPOL 940 ® (neutralized by triethanolamine) | 0.4% |
| Liquid fraction of karite fat | 12% |
| Synthetic perhydrosqualene | 12% |
| Aqueous/alcoholic nutgall extract | 0.1% |
| Ginkgo extract | 1% |
| Sterile demineralized water + preserving agents | q.s. for 100% |

EXAMPLE 3: Hand lotion

| | |
|---|---|
| Ginkgo extract | 1% |
| Green tea extract | 0.1% |
| LECINOL S10 ® | 0.375% |
| GENEROL 122 ES ® | 0.625% |
| D5 (Cyclomethicone) sold by the Company Dow | 2% |
| Glycerol | 10% |
| Methyl parahydroxybenzoate | 0.3% |
| Water | q.s. for 100% |

LECINOL S10® is the commercial name of a hydrogenated lecithin sold by the Company Nikko.

GENEROL 122® ES is the commercial name of a phytosterol, oxyethylenated with 5 mol of ethylene oxide, sold by the Company Henkel.

EXAMPLE 4: Vesicular dispersion

| | |
|---|---|
| Non-ionic amphiphile* | 1.5% |
| Cholesterol | 1.5% |
| Sodium acylglutamate HS21 (Ajinomoto) | 0.5% |
| Glycerol | 10 |
| Green tea extract (SUNPHENON ®) | 0.1% |
| Ginkgo biloba extract | 1% |
| Perhydrosqualene | 10% |
| Methyl parahydroxybenzoate | 0.2% |
| CARBOPOL 940 ® (Goodrich) | 0.4% |
| Triethanolamine     q.s. pH = 7 | |
| Water | q.s. for 100% |

(*) The non-ionic amphiphile is a mixture of products corresponding to the following formula:

$$C_{12}H_{25}-[OC_2H_3(R)-O-C_3H_5(OH)-O]_n-H$$

in which: n, representing the statistical number of units, is equal to 2.7, the —OC$_2$H$_3$(R)— groups represent radicals:

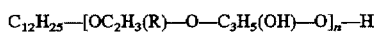

and the —C$_3$H$_5$(OH)—O— groups represent radicals:

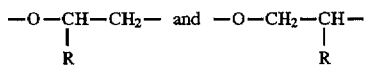

and the R groups represent an equimolar mixture of C$_{14}$H$_{29}$ and C$_{16}$H$_{33}$ radicals.

The product sold under the name "ACYLGLUTAMATE HS21®" is a disodium stearylglutamate.

This vesicular dispersion is prepared in the following way.

The non-ionic amphiphile compound is added to the cholesterol and to the acylglutamate at a temperature of 100° C.

The temperature is lowered to 90° C. and the glycerol, green tea extract, ginkgo extract and water (10 g) are added at this temperature.

The mixture is cooled to 50° C. and then homogenized for 2 times 4 minutes using a VIRTIS 60® homogenizer (at 40,000 rpm).

The product obtained is cooled to room temperature and diluted with 20 g of water. The oily phase (perhydrosqualene and methyl parahydroxybenzoate) is added and the mixture is then homogenized for 2 times 4 minutes at 40,000 rpm.

The CARBOPOL gel (CARBOPOL 940® and water q.s. for 100) is dispersed for 30 seconds at 10,000 rpm and the combined mixture is then neutralized with triethanolamine.

A smooth and glossy cream is obtained. It is used on the scalp to protect the hair from the harmful effects due to free radicals.

STUDY OF THE ANTIOXIDIZING ACTIVITY

The effectiveness of the antioxidizing system according to the invention is demonstrated by the method of accelerated oxidation of vitamin F which is a substance stance particularly sensitive to oxidation.

For the study, the automatic device RANCIMAT® of the Company Metrohm (A. Seher et al., Fette, Seifen, Anstrichmittel, 88(1) 1–6, 1986) is used.

Mixtures of vitamin F with a green tea extract SUNPHENON® alone, with a hexane extract of ginkgo alone and with a mixture of a green tea extract with a hexane extract of ginkgo are prepared.

Each sample is brought to 100° C. while sparging with air (20 liters/h). The concentration of volatile acids resulting from the degradation of the hydroperoxides and aldehydes of vitamin F is then continuously monitored in a cell filled with water in which a platinum electrode is immersed. This electrode measures, as a function of time, the increase in the conductivity caused by the increase in the concentration of volatile acids. The induction time will be determined by the intersection of the two asymptotes of the exponential oxidation curve obtained.

This time corresponds to the latent period preceding self-oxidation of vitamin F. The longer this latent period, the better is the resistance of vitamin F to self-oxidation.

The results are the following:

| Product tested | Induction time |
|---|---|
| Green tea 0.1% | 33 min |
| Ginkgo 1% | 48 min |
| Green tea 0.1% + Ginkgo 1% | 258 min |

I claim:

1. A cosmetic or pharmaceutical composition comprising an antioxidizing system consisting of the combination of a ginkgo extract and at least one polyphenol compound, said ginkgo extract being obtained by extraction of ginkgo leaves with a nonpolar solvent; wherein said polyphenol compound is selected from the group consisting of a flavonoid, carnosic acid, carnosol, a 2,5-dihydroxy benzoic acid, a compound of formula (III)

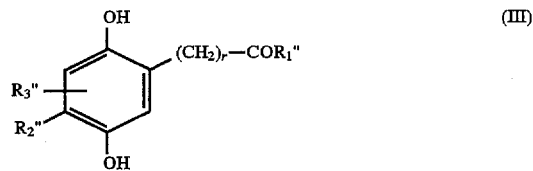

wherein R$_1$" represents —O—Alk, OH or —N(r')(r") wherein Alk represents linear or branched C$_1$–C$_{20}$ alkyl; linear or branched C$_1$–C$_{20}$ alkyl substituted by one or more hydroxyl groups; linear or branched C$_1$–C$_{20}$ alkyl substituted by one or more alkoxy groups, or Alk representing C$_2$–C$_{20}$ alkenyl;

r' and r", each independently represent H, C$_1$–C$_{20}$ alkyl, C$_2$–C$_6$ hydroxyalkyl or C$_3$–C$_6$ polyhydroxyalkyl;

r represents a number, including zero, so that said —(CH$_2$)$_r$—COR$_1$" contains at most 21 carbon atoms; and R$_2$" and R$_3$", each independently, represent H or C$_1$–C$_4$ alkyl, or R$_2$" represents C$_1$–C$_4$ alkoxy, a C$_1$–C$_8$ alkyl ester or caffeic acid, a phytol ester of caffeic acid, a caffeic acid amide of formula (V)

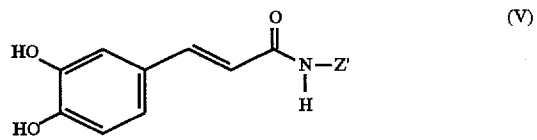

wherein Z' represents C$_1$–C$_8$ alkyl, and tannic acid;

said flavonoids being selected from the group consisting of taxifolin, catechin, epicatechin, eriodictyol, naringenin, rutin, troxerutin, chrysin, tangeretin, luteolin, epigallocatechin, epigallocatechin gallate, quercetin, fisetin, kaempferol, galangin, gallocatechin and epicatechin gallate.

2. The composition of claim 1 wherein said nonpolar solvent is a $C_6$–$C_{14}$ alkane.

3. The composition of claim 1 wherein said nonpolar solvent is n-hexane.

4. The composition of claim 1 wherein said ginkgo extract is present in an amount ranging from 1 to 10 percent by weight based on the total weight of said composition.

5. The composition of claim 1 wherein said polyphenol compound is present in an amount ranging from 0.1 to 1 percent by weight based on the total weight of said composition.

6. The composition of claim 1 wherein the weight ratio of said ginkgo extract to said polyphenol compound ranges from 1 to 100.

7. The composition of claim 1 wherein the weight ratio of said ginkgo extract to said polyphenol compound is in the range of 10.

8. A cosmetic or pharmaceutical composition comprising an antioxidizing system consisting of the combination of a ginkgo extract and at least one polyphenol compound, said ginkgo extract being obtained by extraction of ginkgo leaves with a nonpolar solvent, wherein said polyphenol is selected from the group consisting of a flavonoid, carnosic acid, carnosol, a 2,5-dihydroxybenzoic acid, a compound of formula (III)

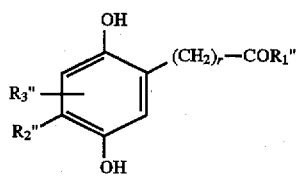

wherein $R_1"$ represents —O—Alk, OH or —N(r')(r") wherein Alk represents linear or branched $C_1$–$C_{20}$ alkyl; linear or branched $C_1$–$C_{20}$ alkyl substituted by one or more hydroxy groups; linear or branched $C_1$–$C_{20}$ alkyl substituted by one or more alkoxy groups, or Alk representing $C_2$–$C_{20}$ alkenyl;

r' and r", each independently represents H, $C_1$–$C_{20}$ alkyl, $C_2$–$C_6$ hydroxyalkyl or $C_3$–$C_6$ polyhydroxyalkyl;

r represents a number, including zero, so that said —$(CH_2)_r$—$COR_1"$ contains at most 21 carbon atoms; and $R_2"$ and $R_3"$, each independently, represents H or $C_1$–$C_4$ alkyl, or $R_2"$ represents $C_1$–$C_4$ alkoxy, a $C_1$–$C_8$ alkyl ester or caffeic acid, a phytol ester or caffeic acid, a caffeic acid amide of formula (V)

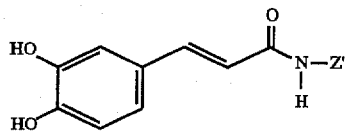

wherein Z' represents $C_1$–$C_8$ alkyl, and tannic acid, wherein said flavonoids are selected from the group consisting of compounds of formula (I) and formula (II)

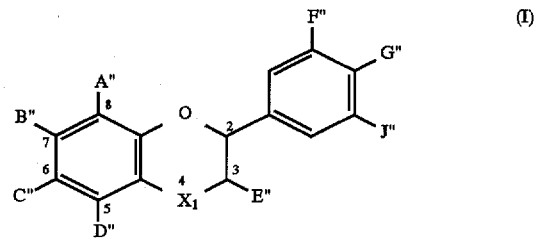

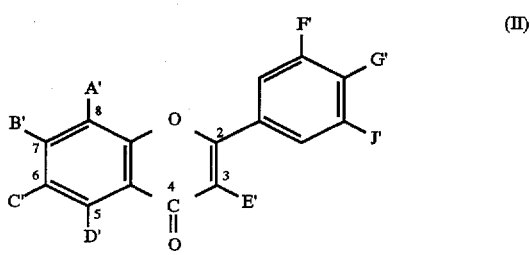

wherein A", B", C" and D", independently of one another, represent H or OH; E" represents H, OH or OX', where X' represents

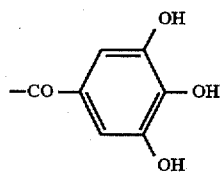

F", G" and J" represent, independently of one another, H or OH; and $X_1$ represents —$CH_2$—, —CO— or —CHOH—;

A', C' and D', independently of one another, represent H, OH or $OCH_3$;

E' represents H, OH or OR', where R' represents a residue of rutinose; and

B', F', G' and J', independently of one another, represent H, OH, $OCH_3$ or —$OCH_2$—$CH_2$—OH.

9. A method of protecting cells of the skin or scalp from damage caused by free radicals induced by atmospheric pollutants or ultraviolet radiation, said method comprising applying to said skin or scalp, the composition of claim 1.

10. A method of protecting cells of the skin or scalp from damage caused by free radicals induced by atmospheric pollutants or ultraviolet radiation, said method comprising applying to said skin or scalp, the composition of claim 8.

11. The composition according to claim 1, wherein said flavonoid is epicatechin.

12. The composition of claim 1, wherein said flavonoid is epicatechin gallate.

13. The composition of claim 1, wherein said flavonoid is epigallocatechin.

14. The composition of claim 1, wherein said flavonoid is epigallocatechin gallate.

* * * * *